United States Patent [19]

Sher

[11] Patent Number: 5,321,036

[45] Date of Patent: Jun. 14, 1994

[54] THIAZOLE AND OXAZOLE-BASED β3 ADRENERGIC RECEPTOR AGONISTS

[75] Inventor: Philip M. Sher, Plainsboro, N.J.

[73] Assignee: Bristol-Myers Squibb Company, Princeton, N.J.

[21] Appl. No.: 15,940

[22] Filed: Feb. 10, 1993

[51] Int. Cl.$^5$ .................... A61K 31/42; C07D 261/08
[52] U.S. Cl. .................................. 514/365; 514/378; 548/201; 548/204; 548/236
[58] Field of Search ................ 514/365, 378; 548/201, 548/204, 236

[56] References Cited

U.S. PATENT DOCUMENTS

| | | |
|---|---|---|
| 3,631,055 | 12/1971 | Posselt et al. . |
| 4,385,066 | 5/1983 | Ainsworth et al. . |
| 4,391,826 | 7/1983 | Mills et al. . |
| 4,438,128 | 3/1984 | Wiedemann et al. ........... 544/277 X |
| 4,585,796 | 4/1986 | Alig et al. . |
| 4,608,383 | 8/1986 | Wiedemann et al. . |
| 4,629,737 | 12/1986 | Cantello . |
| 4,652,679 | 3/1987 | Alig et al. . |
| 4,743,604 | 5/1988 | Alig et al. . |
| 4,753,962 | 6/1988 | Ainsworth et al. . |
| 4,845,127 | 7/1989 | Mills et al. . |
| 4,871,755 | 10/1989 | Alig et al. . |
| 5,064,863 | 11/1991 | Alig et al. . |

FOREIGN PATENT DOCUMENTS

| | | |
|---|---|---|
| 6766 | 1/1980 | European Pat. Off. . |
| 7204 | 1/1980 | European Pat. Off. . |
| 28105 | 5/1981 | European Pat. Off. . |
| 63004 | 10/1982 | European Pat. Off. . |
| 85514 | 8/1983 | European Pat. Off. . |
| 170121 | 2/1986 | European Pat. Off. . |
| 2531312 | 5/1976 | Fed. Rep. of Germany . |

OTHER PUBLICATIONS

R. Howe et al., Selective β3-Adrenergic Agonists of Brown Adipose Tissue and Thermogenesis, 1. [4-[2-[(-2-Hydroxy-3-phenoxypropyl)amino]ethoxy]--phenoxy]acetates, *J. Med. Chem.*, 1992; 35:1751–1759.
R. Howe et al., Selective β3-Adrenegeric Agonists of Brown Adipose Tissue and Thermogenesis. 2. [4-[2-[(-2-Hydroxy-3-phenoxypropyl)amino]ethoxy]-phenoxy]acetamides, *J. Med. Chem.*, 1992; 35:1759–1764.
J. Simiand et al., Antidepresent profile in rodents of SR 58611A, a new selective agonist for a typical b-adrenoceptors, *Eur. J. of Pharmacol.*, 1992; 219:193–201.
D. C. Humber et al., "Disodium (R,R)-5-[2-(3-Chloropheny)-2-hydroxyethyl]amino]propyl]-1,3-benzodioxole-2,2-dicarboxylate (CL 316,243). A Potent β-Adrenergic Agonist Virtually Specific for β3 Receptors. A Promising Antidiabetic and Antiobesity Agent", *J. Med. Chem.*, 1992; 35:3081–3084.

*Primary Examiner*—Mary C. Lee
*Assistant Examiner*—Jacqueline Haley
*Attorney, Agent, or Firm*—Ellen K. Park

[57] ABSTRACT

Compounds having the formula

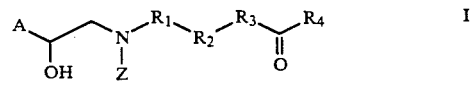

and pharmaceutically acceptable salts thereof where A is

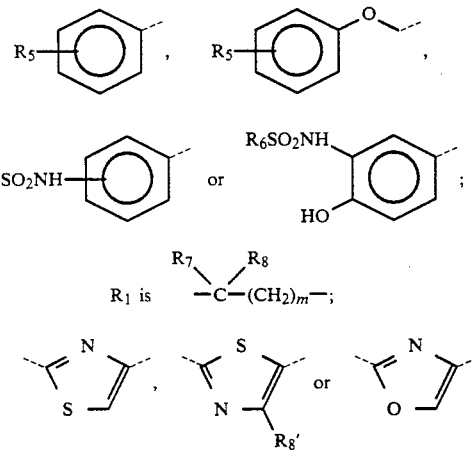

(Abstract continued on next page.)

$R_3$ is $-(CH_2)_n-$ or in the case where $R_2$ is

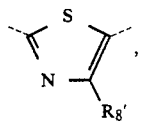, $R_3$ in addition to the above may be

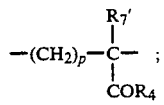

$R_4$ is hydroxy, alkoxy, amino, alkylamino or dialkylamino;

$R_5$ is hydrogen, fluorine, chlorine, bromine, iodine, $-CN$, $CF_3$, lower alkyl, lower alkoxy, cycloalkyl or aryl;

$R_6$ is lower alkyl, cycloalkyl or aryl;

$R_7$, $R_7'$, $R_8$ and $R_8'$ are independently hydrogen or a lower alkyl or $R_7$ and $R_8$ may together be $CH_2CH_2$;

Z is hydrogen or

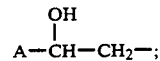;

m is an integer of 1 or 2;

n is zero or an integer of 1 to 6; and p is an integer of 1 to 5. These compounds are beta 3 adrenergic receptor agonists and are useful, therefore for example, in the treatment of diabetes, obesity and gastrointestinal diseases.

31 Claims, No Drawings

THIAZOLE AND OXAZOLE-BASED β3 ADRENERGIC RECEPTOR AGONISTS

BRIEF DESCRIPTION OF THE INVENTION

The present invention is directed to compounds of the formula

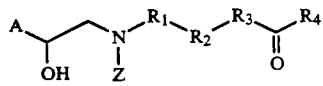

and pharmaceutically acceptable salts thereof. As used in formula I, and throughout the specification, the symbols have the following meanings:

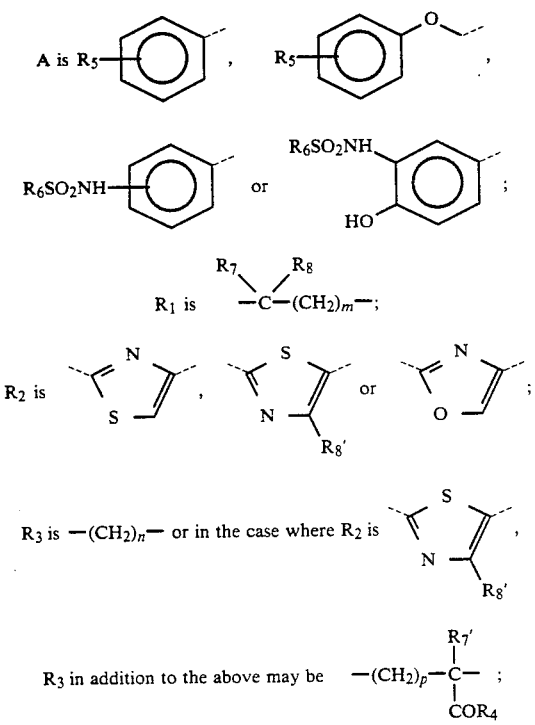

$R_3$ is $-(CH_2)_n-$ or in the case where $R_2$ is 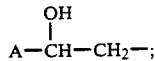

$R_3$ in addition to the above may be
$$-(CH_2)_p-\underset{\underset{COR_4}{|}}{\overset{\overset{R_7'}{|}}{C}}-\ ;$$

$R_4$ is hydroxy, alkoxy, amino, alkylamino or dialkylamino;
$R_5$ is hydrogen, fluorine, chlorine, bromine, iodine, $-CN$, $-CF_3$, lower alkyl, lower alkoxy, cycloalkyl or aryl;
$R_6$ is lower alkyl, cycloalkyl or aryl;
$R_7$, $R_7'$, $R_8$ and $R_8'$, are independently hydrogen or lower alkyl or $R_7$ and $R_8$ may together be $CH_2CH_2$;
Z is hydrogen or $$A-\underset{\underset{}{\overset{\overset{OH}{|}}{C}}H}-CH_2-;$$

m is an integer of 1 or 2;
n is zero or an integer of 1 to 6; and
p is an integer of 1 to 5.

These compounds possess activity at the beta 3 adrenergic receptor. The compounds are useful in the treatment of diabetes, obesity, and intestinal hypermotility disorders. The invention also provides processes for their preparation.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group.

The term "alkyl" refers to both straight and branched chain groups having 1 to 12 carbon atoms in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "lower alkyl" as employed herein includes such alkyl groups as described above containing 1 to 6 carbon atoms in the normal chain.

The term "alkoxy" refers to any of the above alkyl groups linked to an oxygen atom.

The term "lower alkoxy" refers to any of the above lower alkyl groups linked to an oxygen atom.

The term "aryl" refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens (e.g., chlorine, bromine or fluorine), or 1, 2 or 3 lower alkoxy groups.

The term "cycloalkyl" refers to saturated cyclic hydrocarbon groups containing one or more rings of 3 to 12 ring carbons, preferably 3 to 8 ring carbons, which include cyclopropyl, cyclobutyl, cyclopentyl, cyclohexyl, cycloheptyl, cyclooctyl, cyclodecyl, and adamantyl.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I such as aldehyde addition products of formula

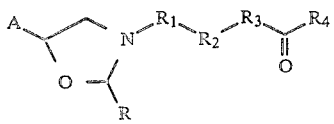
Ia where R is alkyl or aryl such that RCHO is a suitable, for example, non-toxic aldehyde.

The compounds of the instant invention may, for example, be in the free or hydrate form, and may be obtained by methods exemplified by the following descriptions.

Compounds of formula I where A is

$R_2$ is

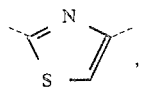

and $R_3$ is —$(CH_2)_n$— may be prepared by coupling a compound of formula

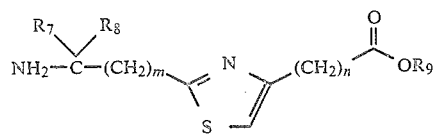
II where $R_9$ is a lower alkyl, with a compound of the formula

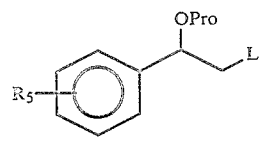
III where Pro is a suitable oxygen protecting group such as t-butyldimethylsilyl and L is a leaving group such as triflate, mesylate, tosylate, nosylate, bromide or iodide, optionally in the presence of an acid scavenger such as diisopropylethylamine to form a compound of formula

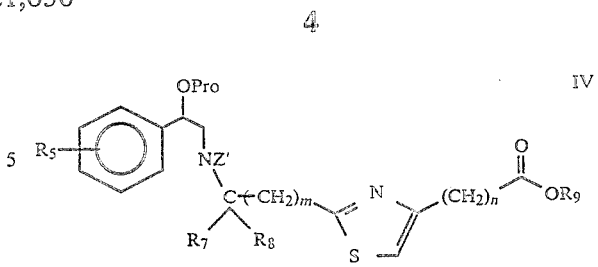
IV where Z′ is hydrogen or

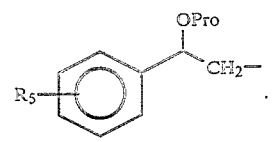

Compounds of formula IV are then deprotected with, for example, fluoride to form compounds of the formula

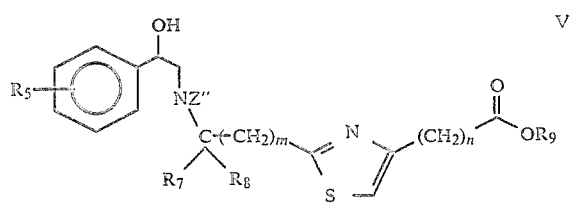
V where Z″ is hydrogen or

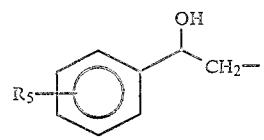

which are themselves compounds of formula I where $R_4$ is alkoxy. Compounds of formula V may be deesterified such as by saponification to form the compounds of formula I where $R_4$ is hydroxy.

Alternatively, compounds of formula V may be amidated, for example with ammonia or a mono or dialkylamine, to form compounds of formula I where $R_4$ is amino, alkylamino or dialkylamino.

Compounds of formula II may also be coupled with an epoxide of formula

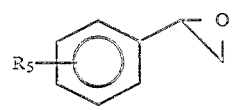
IIIa to form compounds of formula V. Use of epoxide IIIa would obviate the need for the deprotection step as is necessary after coupling compounds of formula II with compounds of formula III.

To prepare compounds of formula I where A is

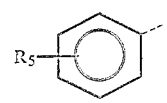

and $R_2$ is

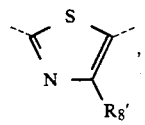

a compound of formula

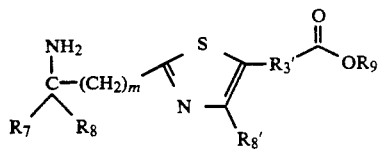

where $R_3'$ is —$(CH_2)_n$— or

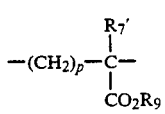

is coupled with a compound of formula III optionally in the presence of an acid scavenger such as diisopropylethylamine to form a compound of formula

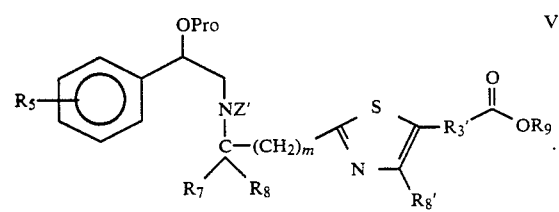

Compounds of formula VII are then deprotected, for example, with fluoride to form compounds of the formula

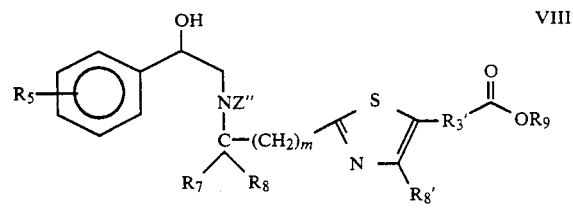

which are themselves compounds of formula I where $R_4$ is alkoxy. Compounds of formula VIII may be deesterified such as by saponification to form the compounds of formula I where $R_4$ is hydroxy.

Alternatively, Compounds of formula VIII may be amidated, for example with ammonia or a mono or dialkylamine, to form compounds of formula I where $R_4$ is amino, alkylamino or dialkylamino.

Compounds of formula VI may also be coupled with an epoxide of formula IIIa to form compounds of formula VIII.

To prepare compounds of formula I where A is

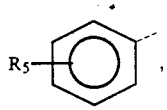

$R_2$ is

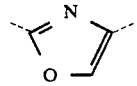

and $R_3$ is —$(CH_2)_n$— a compound of formula

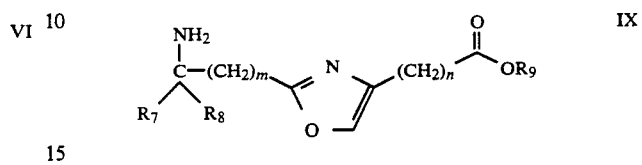

is coupled with a compound of the formula III optionally in the presence of an acid scavenger such as diisopropylethylamine to form a compound of formula

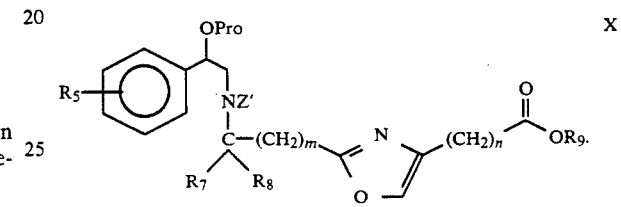

Compounds of formula X are then deprotected, for example, with fluoride to form compounds of the formula

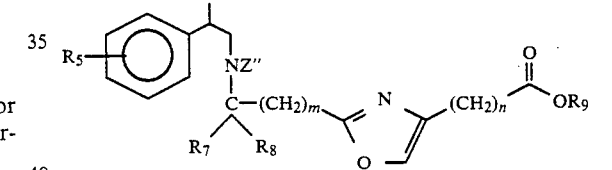

which are themselves compounds of formula I where $R_4$ is alkoxy. Compounds of formula XI may be deesterified such as by saponification to form the compounds of formula I where $R_4$ is hydroxy.

Alternatively, Compounds of formula XI may be amidated, for example with ammonia or a mono or dialkylamine, to form compounds of formula I where $R_4$ is amino, alkylamino or dialkylamino.

Compounds of formula IX may also be coupled with an epoxide of formula IIIa to form compounds of formula XI.

To prepare the compounds of formula I where A is

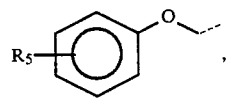

$R_2$ is

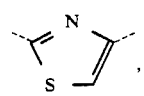

and $R_3$ is —$(CH_2)_n$—, a compound of formula II is coupled with a compound of formula

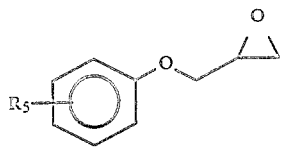

optionally in the presence of a solvent such as 2-propanol or dimethylsulfoxide to form compounds of the formula

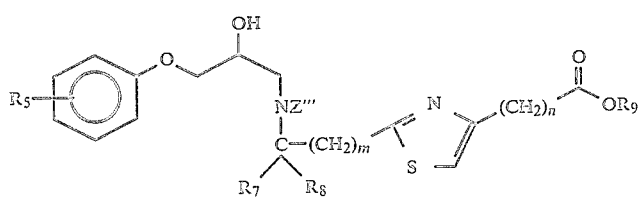

where $Z'''$ is hydrogen or

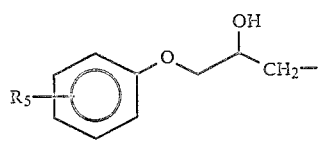

which may then be converted to the compounds of formula I as described above for compounds of formula V.

Compounds of formula I where A is

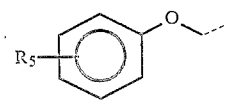

and $R_2$ is

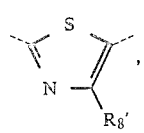

may be prepared by coupling a compound of formula XII with a compound of formula VI optionally in the presence of a solvent such as 2-propanol or dimethylsulfoxide to form compounds of formula

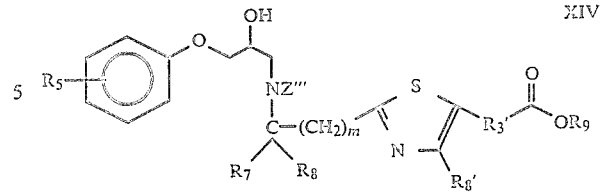

which may then be converted to compounds of formula

XIII as described above for compounds of formula VIII.

To prepare the compounds of formula I where A is

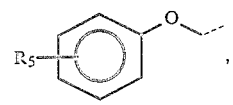

$R_2$ is

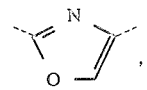

and $R_3$ is $-(CH_2)_n-$, a compound of formula IX is coupled with a compound of formula XII optionally in the presence of a solvent such as 2-propanol or dimethylsulfoxide to form compounds of the formula

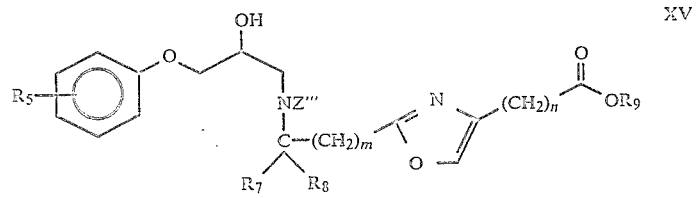

which may then be converted to the compounds of formula I as described above for compounds of formula XI.

Compounds of formula I where A is

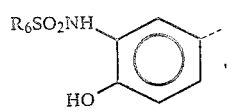

may be prepared by coupling compounds of formulae II, VI or IX with compounds of formula $$\text{R}_6\text{SO}_2\text{NH}\underset{\text{R}_{10}\text{O}}{\overset{}{\bigcirc}}\overset{\text{O}}{\underset{}{\text{C}}}\text{—CH}_2\text{—Br} \qquad \text{XVI}$$

where $R_{10}$ is benzyl or hydrogen, to form compounds of formula $$\text{R}_6\text{SO}_2\text{NH}\underset{\text{R}_{10}\text{O}}{\overset{}{\bigcirc}}\overset{\text{O}}{\underset{}{\text{C}}}\text{—CH}_2\underset{\text{Z}''''}{\overset{}{\text{N}}}\text{—R}_1\text{—R}_2\text{—R}_3'\text{—C(O)OR}_9 \qquad \text{XVII}$$

where $Z''''$ is hydrogen or $$\text{R}_6\text{SO}_2\text{NH}\underset{\text{R}_{10}\text{O}}{\overset{}{\bigcirc}}\overset{\text{O}}{\underset{}{\text{C}}}\text{—CH}_2\text{—}$$

Compounds of formula XVII are subjected to subsequent ketone reduction, and where $R_{10}$ is benzyl, phenol deprotection to form compounds of the formula $$\text{R}_6\text{SO}_2\text{NH}\underset{\text{HO}}{\overset{}{\bigcirc}}\overset{\text{OH}}{\underset{}{\text{CH}}}\text{—CH}_2\underset{\text{Z}'''''}{\overset{}{\text{N}}}\text{—R}_1\text{—R}_2\text{—R}_3'\text{—C(O)OR}_9 \qquad \text{XVIII}$$

where $Z'''''$ is hydrogen or $$\text{R}_6\text{SO}_2\text{NH}\underset{\text{HO}}{\overset{}{\bigcirc}}\overset{\text{OH}}{\underset{}{\text{CH}}}\text{—CH}_2\text{—}$$

Compounds of formula XVI and subsequent chemical methods are known in the art as disclosed in A. A. Larsen et al., *J. Med. Chem.* 10, 462 (1967).

Compounds of formula XVIII themselves are compounds of formula I where $R_4$ is alkoxy. Compounds of formula XVIII may be deesterified, for example by saponification to form compounds of formula I where $R_4$ is hydroxy. Alternatively, compounds of formula XVIII may be amidated, for example with ammonia or a mono or dialkylamine, to form compounds of formula I where $R_4$ is amino, alkylamino or dialkylamino.

Compounds of formula I where A is $$\text{R}_6\text{SO}_2\text{NH—}\bigcirc\text{—}$$

may be prepared from compounds of formulae II, VI, or IX by coupling with compounds of formula $$\text{R}_6\text{SO}_2\text{NH—}\bigcirc\text{—C(O)—CH}_2\text{—Br} \qquad \text{XVIa}$$

and subsequent procedures as outlined immediately above and using methods known in the art (R. H. Uloth, et al., *J. Med. Chem.* 9, 88 (1966)).

Compounds of formula II are prepared by reacting compounds of formula $$\underset{\text{R}_7\quad\text{R}_8}{\overset{\text{BOC—NH}}{\text{C}}}\text{—(CH}_2)_m\text{—C(O)—NH}_2 \qquad \text{XIX}$$

with a thionating reagent such as Lawesson's reagent or Belleau's reagent prepared as described in Lecher, H. Z., et al., *JACS* 78, 5018 (1956) and Belleau, B., et al., *Tet. Lett.* 24, 3815 (1983) to form compounds of formula $$\underset{\text{R}_7\quad\text{R}_8}{\overset{\text{BOC—NH}}{\text{C}}}\text{—(CH}_2)_m\text{—C(S)—NH}_2 \qquad \text{XX}$$

which are then reacted with a haloketone of the formula $$\text{X—CH}_2\text{—C(O)—(CH}_2)_n\text{—CO}_2\text{R}_9 \qquad \text{XXI}$$

where X is chlorine, bromine or iodine, preferably bromine, in a solvent such as ether to form compounds of formula $$\underset{\text{R}_7\quad\text{R}_8}{\overset{\text{BOC—NH}}{\text{C}}}\text{—(CH}_2)_m\overset{\text{OH}}{\underset{\text{S}}{\text{—thiazoline—(CH}_2)_n\text{—CO}_2\text{R}_9}} \qquad \text{XXII}$$

Compounds of formula XXII are then reacted with a dehydrating agent such as methanesulfonyl chloride and triethylamine in an organic solvent such as methylene chloride to form compounds of formula $$\underset{\text{R}_7\quad\text{R}_8}{\overset{\text{BOC—NH}}{\text{C}}}\text{—(CH}_2)_m\overset{}{\underset{\text{S}}{\text{—thiazole—(CH}_2)_n\text{—CO}_2\text{R}_9}} \qquad \text{XXIII}$$

which are then reacted with a deprotecting agent such as trifluoroacetic acid in an organic solvent such as methylene chloride to form the formula II compounds.

In some instances reaction of compounds of formula XX as described above may give compounds of formula XXIII or even compounds of formula II directly.

Compounds of formula XIX are prepared by reacting the appropriate aminoalkanoic acid ester salt, such as (R)-3-aminobutanoic acid methyl ester hydrochloride (prepared as described in U.S. Pat. No. 4,585,887), with a base such as triethylamine and a t-butoxycarbonylating reagent such as di-tert-butyl dicarbonate ((BOC)$_2$O) in an organic solvent such as methylene chloride to form

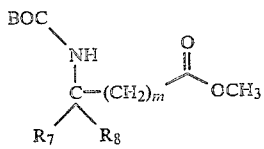
XXIV which is then deesterified with, for example, aq. sodium hydroxide in an organic solvent such as tetrahydrofuran to form compounds of formula

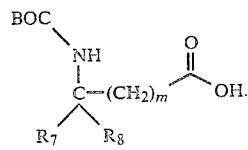
XXV

Compounds of formula XXV are then reacted with ammonia in the presence of a coupling reagent such as 1-hydroxybenzotriazole/1-(3-dimethylaminopropyl)-3-ethylcarbodiimide hydrochloride (WSC) in a solvent such as acetonitrile to form the formula XIX compounds. Compounds of formula XXV may be derived from the appropriate aminoalkanoic acid by t-butoxycarbonylation as described in O. Keller et al., *Org. Synth.* 63, 160 (1984).

Compounds of formula III are prepared by reacting an R$_5$-substituted benzaldehyde with a haloform such as CHBr$_3$ or CHI$_3$ and a lithium salt such as lithium chloride or lithium bromide and an alkali metal hydroxide such as potassium hydroxide or sodium hydroxide in a solvent such as aqueous 1,4-dioxane to form compounds of formula

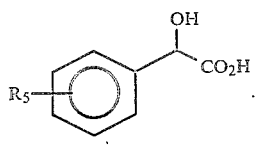
XXVI

Compounds of formula XXVI are then reacted with a methylating agent such as MeI, in the presence of a base such as potassium carbonate in a solvent such as acetone to form

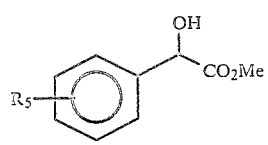
XXVII which are then protected, for example by reaction with tert-butyldimethylsilyl chloride and a base such as imidazole in a solvent such as chloroform, to form compounds of the formula

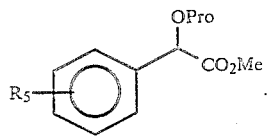
XXVIII

Compounds of formula XXVIII are then reacted with a reducing agent such as diisobutylaluminum hydride in a solvent such as toluene to form

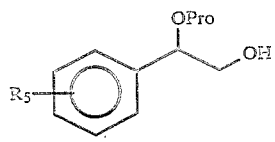
XXIX which are then activated converting the hydroxyl group into a leaving group, for example by reaction with a triflating agent such as Tf$_2$O, in the presence of a base such as pyridine in a solvent such as methylene chloride, to form the compounds of formula III.

Compounds of formula IIIa are prepared from compounds of formula XXVII by standard methods.

Compounds of formula VI may be prepared by reacting a compound of formula

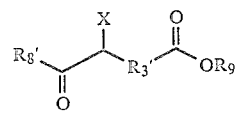
XXX (when R$_3'$ is —(CH$_2$)$_n$— and n is zero, it is preferred that X is chlorine) with a compound of formula XX in the presence of a solvent such as dimethylformamide or 1,2-dichloroethane to form compounds of formula

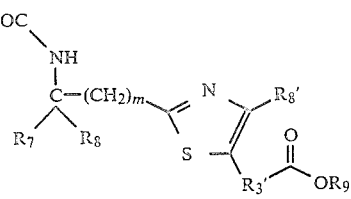
XXXI which are then reacted with a deprotecting agent such as trifluoroacetic acid in a solvent such as methylene chloride to form the formula VI compounds.

Compounds of formula XXX where R$_3'$ is (CH$_2$)$_n$ where n is zero or 1 and R$_8'$ is hydrogen or methyl are all known in the literature. Compounds of formula XXX where R$_8'$ is hydrogen and R$_3'$ is (CH$_2$)$_n$ where n is 2, 3, 4, 5 or 6 may be prepared by reacting the lactone of formula

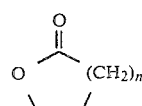
XXXII (known in the art) in an alcohol such as ethanol under acid catalysis with, for example, sulfuric acid followed by treatment with an oxidizing agent such as pyridinium chlorochromate in a solvent such as methylene chloride to form a compound of formula

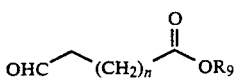   XXXIII which is then reacted with a halogenating agent such as bromine in a solvent such as a mixture of diethyl ether and 1,4-dioxane.

Likewise, compounds of formula XXX where $R_8'$ is a lower alkyl and $R_3'$ is $(CH_2)_n$ where n is 2, 3, 4, 5 or 6 may be prepared by halogenation of compounds of formula

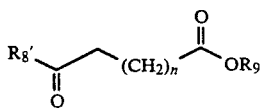   XXXIV with a halogenating agent such as bromine in a solvent such as a mixture of diethyl ether and 1,4-dioxane.

Compounds of formula XXXIV may be made by modifying procedures disclosed in R. Majee et al., *Chemistry and Industry* 167, (1983) and R. Finke et al., *Org. Synth.* 59, 102 (1979).

Compounds of formula XXX where $R_8'$ is hydrogen and $R_3'$ is

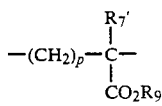

may be prepared by similar halogenation of aldehydes of formula

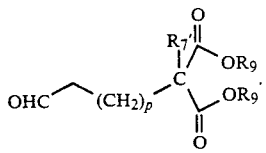   XXXV

Where p is 1, the aldehyde of formula XXXV is prepared by base catalyzed addition of

(known in the art) to acrolein. Where p is 2, the aldehyde of formula XXXV is prepared from the aldehyde of formula XXXV where p is 1 by standard aldehyde homologation procedures such as methoxymethylene Wittig reaction followed by acid catalyzed hydrolysis. Likewise, the aldehyde of formula XXXV where p is 3 may be prepared from the aldehyde of formula XXXV where p is 2. Further repetition of the homologation sequence will provide aldehydes of formula XXXV wherein p is 4 or 5.

Compounds of formula XXX where $R_8'$ is a lower alkyl and $R_3'$ is

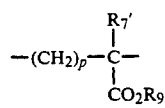

may be prepared analogously to those where $R_8'$ is hydrogen by substituting a lower alkyl vinyl ketone for acrolein.

Compounds of formula IX are prepared by reacting a compound of formula XXV with an amino alcohol of formula

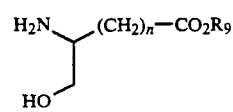   XXXVI in the presence of a coupling agent such as WSC in the optional presence of a catalyst such as 1-hydroxybenzotriazole in a solvent such as MeCN and optionally a base such as triethylamine, to form a compound of formula

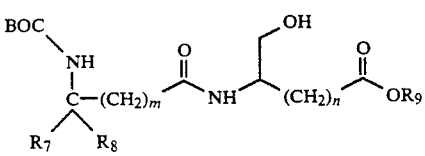   XXXVII which is then reacted with a cyclodehydrating agent such as triphenylphosphine/carbon tetrachloride in the presence of a base such as diisopropylethylamine, in a solvent such as MeCN to form compounds of formula

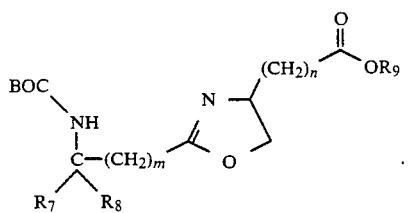   XXXVIII

Compounds of formula XXXVIII are then reacted with an oxidizer such as $CuBr_2$ in the presence of a base such as 1,8-diazabicyclo[5.4.0]undec-7-ene in a solvent such as ethyl acetate/chloroform mixtures to form compounds of formula

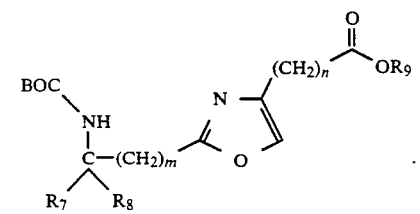   XXXIX

An alternative method includes nickel peroxide oxidation in a solvent such as methylene chloride. Compounds of formula XXXIX are then reacted with a deprotecting agent such as trifluoroacetic acid, optionally in a solvent such as methylene chloride to form the compounds of formula IX.

Compounds of formula XII may be prepared by reacting an activated glycidyl alcohol such as (2S)-(+)- glycidyl 3-nitrobenzenesulfonate with a phenoxide such as sodium phenoxide in an organic solvent such as dimethylformamide.

Compounds of formula XXI for n=0, 1, 2, or 3 are known compounds. In general, compounds of formula XXI may be prepared by halogenation of ketones of formula

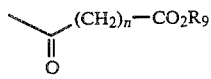  XL which are known in the art, with, for example, bromine in methanol as described in S. F. MacDonald, *Can. J. Chem.* 52, 3258 (1974).

Compounds of formula XXXVI where n is 0, 1, or 2 are known compounds. Higher homologues of the compounds of formula XXXVI may be prepared from the corresponding carboxylic acids $HOCH_2C(NH_2)(CH_2)_nCO_2H$ by acid catalyzed esterification. The carboxylic acids, $HOCH_2C(NH_2)(CH_2)_nCO_2H$, may be prepared from the aminoacids of formula

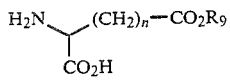  XLI by methods employed in K. Barlos, et al., *J. Chem. Soc. Chem. Commun.* 1583 (1987) and R. B. Silverman and M. A. Levy, *J. Org. Chem.* 45, 815 (1980).

The present compounds of formula I have activity at the beta 3 adrenergic receptor and are therefore useful, for example, in the treatment of diabetes, obesity, and gastrointestinal diseases such as inflammatory bowel disease, irritable bowel syndrome, nonspecific diarrhea, and peptic ulcer.

Thus a composition containing one (or a combination) of the compounds of this invention, may be administered to a species of mammal (e.g., humans) suffering from diabetes, obesity or an intestinal hypermotility disorder as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can also be formulated in combination with beta$_1$/beta$_2$ adrenergic blockers or stimulants.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of depression and stress, regulation of intraocular pressure, treatment of conditions associated with increased protein breakdown such as during convalescence after surgery, treatment of triglyceridemia, hypercholesterolemia, atherosclerotic and cardiovascular diseases, and increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

2-[(R)-2-[[2-(3-chlorophenyl)-2-hydroxyethyl]amino]propyl]-4-thiazolecarboxylic acid A. (R)-3-[[(1,1-Dimethylethoxy)carbonyl]amino]butanoic acid, methyl ester To a solution of (R)-3-aminobutanoic acid, methyl ester (U.S. Pat. No. 4,585,887) in methylene chloride at room temperature under argon was added triethylamine (11.0 g, 109 mmol, 1.1 eq) and di-tert-butyl dicarbonate (23.76 g, 109 mmol, 1.1 eq). The resulting solution warmed upon mixing and was cooled in an ice bath which was then allowed to warm to room temperature. After 16 hours the reaction mixture was concentrated to 70 g and dissolved in a biphasic mixture of ethyl acetate (~500 mL) and water (~500 mL). The organic layer was removed, washed once more with water (~500 mL), dried over sodium sulfate, and concentrated to a yellow oil (29.9 g) which by NMR was shown to consist of 69% desired product. TLC (10% (10% concentrated aq. ammonium hydroxide/methanol)/methylene chloride): 0.83, p-anisaldehyde.

$^{13}$C NMR (67.7 MHz in CDCl$_3$): δ20.1, 28.0, 40.3, 43.2, 51.2, 78.7, 154.8, 171.5.

B. (R)-3-[[(1,1-Dimethylethoxy)carbonyl]amino]butanoic acid

To a solution of the title A compound (13.1 g, 60 mmol) in methanol at room temperature under argon was added ~1M sodium hydroxide (100 mL). After stirring for 60 hours, the solution was acidified at 0° C. to pH 3 by addition of ~1M hydrochloric acid. The resulting solution was extracted four times with ethyl acetate (150 mL). The combined organic layers were dried over sodium sulfate and then concentrated to yield the title compound (12.98 g) as a crystallizing colorless oil, which by proton NMR was shown to be 97% pure title compound.

TLC (2% acetic acid/48% ethyl acetate/50% hexane): 0.6, p-anisaldehyde.

$^{13}$C NMR (67.8 MHz in CDCl$_3$): δ20.4, 28.3, 40.1, 43.3, 79, 155.6, 176.8.

C. (R)-3-[[(1,1-Dimethylethoxy)carbonyl]amino]butanamide

To a solution of the title B compound (4.0 g, 19.7 mmol) in acetonitrile (125 mL) at room temperature under argon was added 1-hydroxybenzotriazole hydrate (2.9 g, 21.7 mmol, 1.1 eq), and WSC (4.1 g, 21.7 mmol, 1.1 eq). After four hours, concentrated aq. ammonium hydroxide (8.1 mL, 118.8 mmol, 6 eq) was added. After stirring overnight the mixture was concentrated to white solid. The solid was chromatographed on silica gel in 75% ethyl acetate/hexane to yield a white solid (3.8 g).

TLC (50% ethyl acetate/hexane): 0.2, p-anisaldehyde, UV.

$^{13}$C NMR (67.8 MHz in CDCl$_3$): δ20.3, 28.2, 42.4, 44.2, 79, 155.8,. 174.7.

D.   2,4-Bis(4-phenoxyphenyl)-2,4-dithioxo-1,3,2,4-dithiadiphosphetane

Made as per description in Lecher, H. Z., et al., *JACS* 78, 5018 (1956) and Belleau, B., et al., *Tet. Lett.*, 24, 3815 (1983).

E.   (R)-3-[[(1,1-Dimethylethoxy)carbonyl]amino]-butanethioamide (See Belleau, B., et al., *Tet. Lett.* 24, 3815, (1983) for examples of thionations involving BOC-protected amides.)

To a solution of the title C compound (~1 g, ~5.0 mmol) in tetrahydrofuran (40 mL) under argon at room temperature was added the title D compound (1.45 g, 2.8 mmol, ~0.6 eq). The solution was stirred for two hours, after which another 480 mg (0.2 eq) of the title D compound was added. The reaction was complete by TLC at four hours. The solution was concentrated and then chromatographed on silica gel in ethyl acetate/hexane (1:1) to isolate the desired product as a white solid (750 mg).

TLC (30% acetone/toluene): 0.6, p-anisaldehyde, UV.

$^{13}$C NMR (67.8 MHz in CDCl$_3$): δ19.8, 28.0, 45.9, 53.2, 78, 155.8, 206.8.

F.   (R)-4,5-Dihydro-2-[2-[[(1,1-dimethylethoxy)carbonyl]-amino]propyl]-4-hydroxy-4-thiazolecarboxylic acid, ethyl ester See Houssin, R., et al., *JOC*, 50, 2788 (1985), for similar condensations. See U.S. Pat. No. 5,100,889 for examples of similar hydroxy-thiazoline-intermediates.

A solution of the title E compound (310 mg, 1.4 mmol) and ethyl bromopyruvate (0.18 mL, 1.4 mmol, 1.0 eq) in diethyl ether (15 mL) stirred at room temperature under argon overnight yielded a white precipitate. The mixture was added to ice water (~40 mL) and basified to pH 11 by addition of concentrated aq. ammonium hydroxide. The organic layer was removed and the aqueous layer was extracted four times with methylene chloride (30 mL). The combined organic layers were dried over sodium sulfate and then concentrated to give a clear, colorless oil (450 mg).

TLC (10% concentrated aq. ammonium hydroxide/methanol)/methylene chloride): 0.6, p-anisaldehyde, UV.

G.   (R)-2-[2-[[(1,1-Dimethylethoxy)carbonyl]amino]-propyl]-4-thiazolecarboxylic acid, ethyl ester To a solution of the title F compound (427.8 mg, 1.3 mmol) in methylene chloride under argon at −78° was added triethylamine (723 μL, 7.2 mmol, 5.5 eq). Methanesulfonyl chloride (151 μL, 1.95 mmol, 1.5 eq) was added over one minute. The reaction was complete by TLC in 20 minutes. Methanol (~20 mL) was added and the resulting solution was concentrated and chromatographed on silica gel in 30% ethyl acetate/hexane to yield a yellow oil (400 mg).

TLC (50% ethyl acetate/hexane): 0.4, p-anisaldehyde, UV.

$^{13}$C NMR (67.8 MHz in CDCl$_3$): δ14.0, 20.3, 28.0, 39.8, 46.5, 61.0, 80.1, 127.4, 146.7, 154.8, 161.1, 167.7.

H.   (R)-2-(2-Aminopropyl-4-thiazolecarboxylic acid, ethyl ester

To a solution of the title G compound (384 mg, 1.2 mmol) in methylene chloride (~15 mL) at room temperature was added trifluoroacetic acid (~15 mL). After three hours the solution was concentrated and redissolved in methylene chloride (~25 mL), to which was added ~1M sodium bicarbonate (25 mL) and brine (30 mL). The mixture was extracted three times with methylene chloride (25 mL), and the combined extracts were dried over sodium sulfate, and concentrated. The resulting oil was chromatographed in 8% (10% concentrated aq. ammonium hydroxide/methanol)/methylene chloride to isolate desired products as a clear oil (200 mg).

TLC (10% (10% concentrated aq. ammonium hydroxide/methanol)/methylene chloride): 0.6, p-anisaldehyde, UV.

—C NMR (67.8 MHz in CDCl$_3$): δ14.0, 23.3, 43.0, 47.0, 60.9, 127.0, 146.4, 160.9, 168.7.

I. 3-Chloro-α-hydroxybenzeneacetic acid

To a mixture of lithium chloride (29.9 g, 705 mmol, 2 eq), potassium hydroxide (79.9 g, 1.42 mol, 4 eq), and ice (316 g) stirring in an ice bath was added 1,4-dioxane (158 mL), bromoform (90 g, 356 mmol, 1 eq), and m-chlorobenzaldehyde (50 g, 356 mmol). The mixture was allowed to warm to room temperature and the resulting clear yellow biphasic mixture was stirred at room temperature for 60 hours. The mixture was then heated at 55° C. to 60° C. for 36 hours and cooled to room temperature. The organic layer was removed and the aqueous layer was washed three times with ethyl acetate (200 mL). The aqueous layer was acidified at 0° C. to pH 1 by addition of ~1M hydrochloric acid. The acidic solution was extracted three times with ethyl acetate (300 mL). The ethyl acetate layers were combined, dried over sodium sulfate, and concentrated to a white solid (25.5 g).

TLC (2% acetic acid/48% ethyl acetate/hexane): 0.2, p-anisaldehyde, UV.

—C NMR (67.8 MHz in CDCl$_3$): δ72.3, 124.9, 127.5, 128.0, 129.9, 134.5, 141.5, 174.8.

J. 3-Chloro-α-hydroxybenzeneacetic acid, methyl ester

To a solution of the title I compound (25.0 g, 135 mmol) in acetone (350 mL) stirring mechanically at room temperature under argon was added potassium carbonate (106.3 g, 769 mmol, 5.7 eq). MeI (22.1 mL, 358 mmol, 2.7 eq) was added in three aliquots over ten minutes. After stirring for ten minutes, the mixture was heated to a slow reflux which was maintained for 2.5 hours. The mixture was filtered and the filtrate was concentrated to a yellow oil, which was then chromatographed on silica gel in 10% ethyl acetate/hexane to isolate a white solid (41.3 g containing 24.4 g of the title compound).

TLC (10% ethyl acetate/hexane): 0.65, p-anisaldehyde, UV.

—C NMR (67.8 MHz in CDCl$_3$): δ52.9, 72.1, 124.6, 126.6, 128.4, 129.6, 134.2, 140.0, 173.3.

K. 3-Chloro-α-[[(1,1-dimethylethyl)dimethylsilyl]oxy]-benzeneacetic acid, methyl ester To a solution of the title J compound (19.07 g, 96 mmol) and imidazole (3.63 g, 53 mmol, 0.6 eq) in chloroform (~100 mL) stirring at room temperature under argon was added tert-butyldimethylsilyl chloride (9.91 g, 66 mmol, 0.69 eq). After stirring overnight, another 0.69 eq of each reagent was added to the mixture, which was then stirred for four hours. Hexane (~200 mL) was added to the mixture. Filtration followed by concentration of the resulting filtrate resulted in a yellow oil which was then chromatographed on silica gel in 5% ethyl acetate/hexane to obtain a clear, colorless oil (24.5 g).

TLC (20% acetone/toluene): 0.9, PMA stain, UV.

—C NMR (67.8 MHz in CDCl$_3$): δ—5.3, —5.2, 18.3, 25.6, 52.3, 73.7, 124.4, 126.4, 128.2, 129.6, 134.3, 141.0, 172.0.

L. 3-Chloro-β-[[(1,1-dimethylethyl)dimethylsilyl]oxy]-benzeneethanol

A solution of the title K compound (9.9 g, 31.5 mmol) in toluene (~75 mL) was added to an argon purged 2 L three-neck flask and then chilled to 0° C. Diisobutylaluminum hydride (1.5M in toluene, 53 mL, 79.6 mmol, 2.5 eq) was added dropwise over ~15 minutes. After one hour the reaction mixture was quenched at 0° C. by slow addition of acetone (~100 mL). Silica gel (80 g, premixed with 42 mL water to form a free-flowing powder) was added portionwise, with noticeable gas evolution. About 800 mL acetone was added alternately with the silica gel to keep the reaction slurry stirrable. The mixture was filtered (acetone rinse), and the filtrate was concentrated to a clear oil. Chromatography on silica gel in 8% acetone/toluene yielded a clear colorless oil (7.85 g).

TLC (20% acetone/toluene): 0.7, PMA stain, UV.

—C NMR (67.8 MHz in CDCl$_3$): δ—5.1, —4.9, 18.0, 25.6, 68.4, 75.0, 124.2, 126.2, 127.5, 129.3, 133.9, 143.7.

M. 3-Chloro-β-[[(1,1-dimethylethyl)dimethylsilyl]oxy]-benzeneethanol, (trifluoromethyl)sulfonate To a solution of the title L compound (2.0 g, 6.9 mmol) in methylene chloride (40 mL) under argon at 0° C. was added pyridine (841 mL, 10.4 mmol, 1.5 eq). Triflic anhydride (1.21 mL, 7.2 mmol, 1.05 eq) was added over ~two minutes. After 10 minutes the mixture was diluted with ~50 mL ether, and then washed twice with 50 mL ~1M hydrochloric acid, twice with 50 mL water, and twice with 50 mL of brine. The organic layer was dried over sodium sulfate, and concentrated to an orange oil (2.6 g).

TLC (15% ethyl acetate/hexane): 0.75, p-anisaldehyde, UV.

—C NMR (67.8 MHz in CDCl$_3$): δ—5.0, —4.6, 18.2, 25.8, 68.7, 75.2, 124.3, 126.4, 127.8, 129.5, 134.2, 143.7.

N. 2-[(R)-2-[[2-(3-Chlorophenyl)-2-[[(1,1dimethylethoxy)-dimethylsilyl]oxy]ethyl]amino]propyl]-4-thiazolecarboxylic acid, ethyl ester Couplings of related compounds are described in Bernauer, C., et al., Helv. Chim. Acta. 71, 320 (1988).

To a solution of the title H compound (35 mg, 0.16 mmol) in CD$_3$CN (0.75 mL) at room temperature under argon was added diisopropylethylamine (28 μL, 20.6 mg, 0.16 mmol, 1 eq), and the title M compound (66 mg, 0.16 mmol). After 18 hours concentration and silica gel chromatography in 5% (10% concentrated aq. ammonium hydroxide/methanol)/methylene chloride provided the title N compound.

TLC (10% (10% concentrated aq. ammonium hydroxide/methanol)/methylene chloride): 0.75, p-anisaldehyde, UV.

O. 2-[(R)-2-[[2-(3-Chlorophenyl)-2-hydroxyethyl]amino]propyl]-4-thiazolecarboxylic acid, ethyl ester To a solution of the title N compound (120 mg, 0.25 mmol) in tetrahydrofuran (~5 mL) was added tetrabutylammonium fluoride (1.0M in tetrahydrofuran, 750 μL, 0.75 mmol, 3 eq). The resulting solution was stirred overnight at room temperature. The reaction solution was then concentrated and chromatographed in 8% (10% concentrated aq. ammonium hydroxide/methanol/methylene chloride) to isolate desired product as a yellow oil (78 mg).

TLC (10% (10% concentrated aq. ammonium hydroxide/methanol)/methylene chloride): 0.5, p-anisaldehyde, UV.

P. 2-[(R)-2-[[2-(3-Chlorophenyl)-2-hydroxyethyl]amino]propyl]-4-thiazolecarboxylic acid To a solution of the title O compound (37 mg, 0.10 mmol) in methanol (0.6 mL) at room temperature was added aqueous sodium hydroxide solution (~1M, 330 μL, ~3 eq). The mixture was stirred overnight at room temperature before quenching by addition of acetic acid (glacial, 29 μL, 0.5 mmol, 5 eq). After concentration the resulting oil was chromatographed on a Sep-Pak "Classic" C$_{18}$-cartridge, eluting first with water to remove excess acetic acid and sodium acetate, then with 20% to 40% methanol/water to elute desired product which was obtained as a fluffy, white lyophilate (18 mg).

TLC (20% methanol/1% acetic acid/79% methylene chloride): 0.3 (very streaky), p-anisaldehyde, UV.

High resolution MS: observed: 341.0739 (M+H)$^+$, calculated: 341.0727 (M+H)$^+$; m.p. 128° C. to 130° C.

EXAMPLE 2

[S-(R*,S*)]-2-[2-[2-hydroxy-3-phenoxypropyl)amino]-propyl]-4-thiazolecarboxylic acid A. (S)-(Phenoxymethyl)oxirane The title compound was prepared by the procedures described in Klunder, J. M., et al., JOC 54, 1302 (1989) in 59% yield (87.9% ee).

TLC (10% methanol/methylene chloride): 0.9, p-anisaldehyde, UV.

—C NMR (67.8 MHz in CDCl$_3$): δ44.5, 50.0, 68.5, 114.5, 121.0, 129.4, 158.3.

B. [S-(R*,S*)]-2-[2-[(2-Hydroxy-3-phenoxypropyl)amino]propyl]-4-thiazolecarboxylic acid, ethyl ester To a solution of the title H compound of Example 1, (R)-2-(2-aminopropyl)-4-thiazolecarboxylic acid, ethyl ester (92 mg, 0.43 mmol) in isopropanol (~1 mL) was added the title A compound (65 mg, 0.43 mmol). After four hours, the yellow solution was concentrated to ¼ its initial volume, and allowed to stir at room temperature for two days. Chromatography in 2% methanol/0.5% concentrated aq. ammonium hydroxide/97.5% methylene chloride yielded pure title compound (58 mg). The corresponding bis-alkylated product (62 mg) was also isolated from the column.

TLC (10% (10% concentrated aq. ammonium hydroxide/methanol)/methylene chloride): 0.5, p-anisaldehyde, UV.

—C NMR (67.8 MHz in CDCl$_3$): δ14.3, 20.5, 40.5, 49.0, 52.9, 61.4, 68.4, 70.2, 114.5, 121.0, 127.4, 129.4, 146.6, 158.8, 162.5, 168.8.

C. [S-(R*,S*)]-2-[2-[2-[(2-Hydroxy-3-phenoxypropyl)amino]-propyl]-4-thiazolecarboxylic acid To a solution of the title B compound (35 mg, 0.10 mmol) in methanol (0.5 mL) was added aq. sodium hydroxide (~1M, 300 μL, 0.3 mmol, 3 eq). The reaction was quenched at one hour by addition of acetic acid (glacial, 29 μL, 0.5 mmol, 5 eq). After concentration the resulting oil was chromatographed on a Sep-Pak "Classic" C$_{18}$-cartridge, eluting first with water to remove excess acetic acid and sodium acetate, then with 20% to 40% methanol/water to elute desired product which was obtained as 40 mg of fluffy, white lyophilate.

TLC (10% methanol/1% acetic acid/89% methylene chloride): 0.1 (very streaky), p-anisaldehyde, UV.

High resolution MS: Found: 337.1219 (M+H)+. Calculated: 337.1222 (M+H)+.

Opt. Rot. $[\alpha]_D = -1127.8$ (c=0.09 in methanol); m.p. 96° C. to 100° C.

EXAMPLE 3

[S-(R*,S*)]-2-[2-[(2-hydroxy-3-phenoxypropyl)amino]propyl]-5-thiazolepropanoic acid A. 5-Oxopentanoic acid, ethyl ester See Huckstep, M. and Taylor, R. J. K., *Synthesis* 881 (1982), for a synthesis of methyl 5-oxopentanoate using this method. See Cainelli, G., Manescalchi, F., Umani-Ronchi, A., and Panunzio, M., *JOC* 43, 1598 (1978) for a synthesis of this compound using different chemistry.

To a solution of δ-valerolactone (mw 100.1, 10.0 g, 0.100 mol) in absolute ethanol (200 mL) was added concentrated sulfuric acid (10 drops). The solution was refluxed for four hours, and left standing at room temperature under argon for 60 hours. The solution was neutralized by addition of sodium bicarbonate (1 g). All solids were filtered from the neutralized mixture. The filtrate was then concentrated on a rotary evaporator using a room temperature water bath. After the ethanol was removed from the solution, the residue was dissolved in methylene chloride. To this solution was added pyridinium chlorochromate (mw 216, 31 g, 144 mmol, 1.4 eq). After 40 minutes, the reaction was incomplete with respect to starting material, but was worked up by dilution with ether (~200 mL) and filtration through a pad of Florisil four inches in diameter and six inches deep. The filtrate was concentrated and chromatographed on silica gel in 10% ether/pentane to yield a clear oil (3.12 g, 72% pure desired product).

TLC (50% ether/pentane): $R_f$=0.65, PMA stain.

B. 4-Bromo-5-oxopentanoic acid, ethyl ester

See U.S. Pat. No. 4,053,618 for a similar bromination.

To a solution of the title A compound (3.1 g, 72% pure, 15.6 mmol) in ether (24 mL)/1,4-dioxane (2.4 mL) at room temperature under argon was added bromine (mw 160, 128 mg, 0.8 mmol, 0.1 eq). The solution was immediately cooled to 0° C., and then another 1.13 g of bromine was (7.1 mmol, 0.9 eq) was added. Another 0.5 eq (614 mg) of bromine was added. The reaction solution did not quite decolorize, and the reaction did not appear to go to completion by TLC. The solution was poured into saturated aq. sodium bicarbonate (~40 mL), and after mixing, the organic layer was removed. The aqueous layer was then extracted three times with methylene chloride (~40 mL). The combined organic layers were dried (sodium sulfate), and concentrated to a yellow oil (3.03 g), ~45% pure desired product.

TLC (30% ethyl acetate/hexane): $R_f$=0.56, p-anisaldehyde.

C. (R)-2-[2-[[(1,1-Dimethylethoxy)carbonyl]amino]propyl]-5-thiazolepropanoic acid, ethyl ester A solution of crude title B compound (3.03 g, ~45% pure, ~6.1 mmol) and the title E compound of Example 1, (R)-3-[[(1,1-dimethylethoxy)carbonyl]amino]butanethioamide (700 mg, 3.2 mmol), in dichloroethane (~40 mL) was refluxed under argon overnight. The dark brown reaction solution was poured into ice water (20 mL) which had been basified to pH 11-12 by addition of concentrated aq. ammonium hydroxide. The mixture was then extracted five times with methylene chloride (~40 mL), and the combined organic layers were dried over sodium sulfate. After concentration, the resulting brown oil was chromatographed on silica gel in 20% ethyl acetate/hexane to isolate the desired product as a brown oil (270 mg).

TLC (20% acetone/toluene): $R_f$=0.45, p-anisaldehyde, UV.

13C NMR (67.8 MHz in CDCl₃): δ14.0, 20.1, 22.1, 28.3, 35.6, 39.4, 46.3, 60.5, 79, 137.7, 137.7, 155.0, 165.6, 171.8.

D. (R)-2-(2-Aminopropyl)-5-thiazolepropanoic acid, ethyl ester

To a solution of the title C compound (270 mg, 0.8 mmol) in methylene chloride (~10 mL) under argon was added trifluoroacetic acid (~10 mL). The resulting solution was stirred at room temperature overnight. After concentration, the residual oil was dissolved in chloroform (~30 mL). This solution was then washed with brine (~30 mL) which had been basified to pH 12 by addition of concentrated aq. sodium hydroxide. The organic layer was removed and the remaining aqueous layer was then extracted six times with methylene chloride. The combined organic layers were dried over sodium sulfate and chromatographed on silica gel in 10% (10% concentrated aq. ammonium hydroxide/methanol)/methylene chloride to isolate title compound as a crystallizing brown oil (226 mg).

TLC (10% (10% concentrated aq. ammonium hydroxide/methanol)/methylene chloride): $R_f$=0.25, p-anisaldehyde, UV.

13C NMR (67.8 MHz in CDCl₃): δ13.9, 22.1, 22.7, 35.4, 42.4, 47.2, 60.4, 136.6, 137.5, 166.7 171.7.

E. [S-(R*,S*)]-2-[2-[(2-Hydroxy-3-phenoxypropyl)amino]propyl]-5-thiazolepropanoic acid, ethyl ester To a solution of the title D compound (123 mg, 0.5 mmol) in isopropanol (~1 mL) at room temperature under argon was added the title A compound of Example 2, (S)-(Phenoxymethyl)oxirane (78 mg, 0.5 mmol). After four days, the yellow solution was concentrated and chromatographed on silica gel in 5% (10% concentrated aq. ammonium hydroxide/methanol)/methylene chloride to yield pure title compound (15 mg). (65 mg of the corresponding bis-alkylated compound was also isolated).

TLC (10% (10% concentrated aq. ammonium hydroxide/methanol)/methylene chloride): $R_f$=0.44, p-anisaldehyde, UV.

13C NMR (67.8 MHz in CDCl₃): δ14.1, 20.4, 22.3, 35.7, 40.1, 48.8, 52.6, 60.7, 68.1, 70.1, 114.5, 120.9, 129.4, 137, 139.4, 158, 167, 172.

F. [S-(R*,S*)]-2-[2-[(2-hydroxy-3-phenoxypropyl)amino]propyl]-5-thiazolepropanoic acid To a solution of the title E compound (22 mg, 0.06 mmol) in methanol (~3 mL) at room temperature was added aq. sodium hydroxide (~1M, 180 μL, 0.18 mmol, 3 eq). The resulting solution was allowed to stir for 60 hours before the addition of acetic acid (glacial, 17 μL, 0.30 mmol, 5 eq). The reaction solution was lyophilized and chromatography on a Sep-Pak "Classic" cartridge (eluting with 10% methanol/water) gave after lyophilization the title compound (27 mg) containing 0.25 moles of acetate.

TLC (20% methanol/1% acetic acid/79% methylene chloride): $R_f$=0.07 (very streaky), p-anisaldehyde, UV.

High resolution MS: observed: 365.1522 (M+H)+, calculated: 365.1535 (M+H)+; m.p. 68° C. to 72° C.

EXAMPLE 4

[2R-[2R*(S*,S*)]]-2-[2-[Bis(2-hydroxy-3-phenoxypropyl)amino]propyl]-5-thiazolepropanoic acid To a solution of the bis-alkylated side-product isolated in the preparation of the title E compound of Example 3 (55 mg, 0.10 mmol) in methanol (~5 mL) at room temperature was added aq. sodium hydroxide (~1M, 300 μL, 0.3 mmol, 3 eq). The resulting solution was allowed to stir for 60 hours before addition of acetic acid (glacial, 21 μL, 0.37 mmol, 3.7 eq). The reaction solution was concentrated and then silica gel chromatography, eluting with 10% methanol/1% acetic acid/89% methylene chloride provided the title compound as a white oil (46 mg) containing 0.45 moles of sodium acetate.

TLC (10% methanol/1% acetic acid/89% methylene chloride): 0.18, p-anisaldehyde, UV.

High resolution MS: observed: 515.2207 $(M+H)^+$, calculated: 515.2206 $(M+H)^+$; m.p. 127° C. to 135° C.

Elemental Analysis (%): Calc'd: C 60.71; H 6.54; N 5.07; Found: C 60.53; H 6.24; N 4.77.

EXAMPLE 5

2-[(R)-2-[[2-(3-Chlorophenyl)-2-hydroxyethyl]amino]propyl]-5-thiazolepropanoic acid A. 2-[(R)-2-[[2-(3-Chlorophenyl)-2-[[(1,1-dimethylethoxy)-dimethylsilyl]oxy]ethyl]amino]propyl]-5-thiazolepropanoic acid, ethyl ester To a solution of the title D compound of Example 3 (58 mg, mw 242, 0.24 mmol) in $CD_3CN$ (~1 mL) under argon at room temperature was added diisopropylethylamine (mw 129.3, d 0.74, 42 μL, 31 mg, 0.24 mmol, 1.0 eq), and the title M compound of Example 1 (100 mg, mw 419, 0.24 mmol, 1.0 eq). The solution was stirred 24 hours. The solution was concentrated and chromatographed on silica gel once in 1% concentrated aq. ammonium hydroxide/5% methanol/94% methylene chloride and again in 30% ethyl acetate/hexane to yield pure title compound (45 mg).

TLC (50% ethyl acetate/hexane): $R_f=0.3$, p-anisaldehyde, UV.

B. 2-[(R)-2-[[2-(3-Chlorophenyl)-2-hydroxyethyl]amino]propyl]-5-thiazolepropanoic acid, ethyl ester To a solution of the title A compound (45 mg, f.w. 511, 0.09 mmol) at room temperature under argon in tetrahydrofuran (~4 mL) was added acetic acid (17M, 18 μL, 0.31 mmol, 3.4 eq), and tetrabutylammonium fluoride (Aldrich, 1M in tetrahydrofuran, 310 μL, 0.31 mmol, 3.4 eq). The solution was stirred overnight, and another 3 eq each of acetic acid and tetrabutylammonium fluoride were added. The solution was stirred for a total of 60 hours, and was then concentrated and chromatographed on silica gel in 5% (10% concentrated aq. ammonium hydroxide/methanol)/methylene chloride to isolate a pure title compound (28 mg).

TLC (10% (10% concentrated aq. ammonium hydroxide/methanol)/methylene chloride): $R_f=0.4$, p-anisaldehyde, UV.

C. 2-[(R)-2-[[2-(3-Chlorophenyl)-2-hydroxyethyl]amino]propyl]-5-thiazolepropanoic acid To a solution of the title B compound (26 mg, f.w. 396, 0.07 mmol) in methanol (~1 mL) at room temperature was added aq. sodium hydroxide (~1M, 210 μL, 0.210 mmol, 3 eq). The resulting solution was allowed to stir 18 hours before quenching by addition of acetic acid (glacial, 18 μL, 0.32 mmol, 1.5 eq with respect to sodium hydroxide). The reaction solution was lyophilized and then chromatography on a Sep-Pak "Classic" $C_{18}$-cartridge (eluting with 30% methanol/water) provided the title compound as a white lyophilate (20 mg).

TLC (1% acetic acid/10% methanol)/89% methylene chloride): $R_f=0.09$, p-anisaldehyde, UV.

High resolution MS: observed: 369.1058 $(M+H)^+$, calculated: 369.1040 $(M+H)^+$.

EXAMPLE 6

2-[(R)-2-[[2-(3-Chlorophenyl)-2-hydroxyethyl]amino]propyl]-4-oxazolecarboxylic acid A. (R)-N-[3-[[(1,1-Dimethylethoxy)carbonyl]amino]-1-oxobutyl]-L-serine, methyl ester To a solution of the title B compound of Example 1 (4.0 g, mw 203, 19.7 mmol) in MeCN (~125 mL) stirring at room temperature under argon was added 1-hydroxybenzotriazole (mw 135.1, 2.93 g, 21.7 mmol, 1.1 eq) and WSC (mw 191.2, 4.1 g, 21.4 mmol, 1.1 eq). After two hours triethylamine (mw 101.1, d 0.73, 3.0 mL, 2.2 g, 21.7 mmol, 1.1 eq) was added, followed by L-serine methyl ester hydrochloride salt (mw 155.6, 3.39 g, 21.8 mmol, 1.1 eq). After stirring overnight, the solution was concentrated and chromatographed in 10% (10% concentrated aq. ammonium hydroxide/methanol)/methylene chloride to isolate pure desired product as a white powder (4.9 g).

TLC (10% methanol/35% ethyl acetate/55% hexane): $R_f=0.4$, p-anisaldehyde.

$^{13}C$ NMR (67.8 MHz in $CDCl_3$): δ171.4, 170.8, 155.4, 79.1, 62.1, 54.5, 52.1, 44.1, 42.4, 28.1, 20.4.

B. (R)-2-[2-[[(1,1-Dimethylethoxy)carbonyl]amino]propyl]-4,5-dihydro-4-oxazolecarboxylic acid, methyl ester To a solution of the title A compound (4.9 g, mw 304, 16.2 mmol) in acetonitrile (80 mL) under argon in a room temperature water bath was added triphenylphosphine (mw 262.3, 13.11 g, 50.0 mmol, 3.1 eq), diisopropylethylamine (mw 129.3, d 0.742, 8.7 mL, 6.5 g, 50.0 mmol, 3.1 eq), and carbon tetrachloride (mw 153.8, d 1.6, 4.8 mL, 7.7 g, 50.1 mmol, 3.1 eq). The solution was stirred overnight before it was diluted with ethyl acetate (~100 mL). Aqueous sodium bicarbonate (~1M, 70 mL) was added. The mixture was extracted five times with methylene chloride (75 mL), and the organic layers were then combined and dried over sodium sulfate. Concentration and chromatography on silica gel eluting with 5% (10% concentrated aq. ammonium hydroxide/methanol)/methylene chloride gave a brown solid (13.8 g) consisting of 70% triphenylphosphine oxide and 30% desired product.

TLC (10% (10% concentrated aq. ammonium hydroxide/methanol)/methylene chloride): $R_f=0.25$, p-anisaldehyde.

$^{13}C$ NMR (67.8 MHz in $CDCl_3$): δ172.6, 168.6, 156.0, 79, 70.2, 68.9, 52.9, 45.0, 35.3, 28.6, 20.6.

C. (R)-2-[2-[[(1,1-Dimethylethoxy)carbonyl]amino]propyl]-4-oxazolecarboxylic acid, methyl ester A solution of 1,8-diazabicyclo[5.4.0]undec-7-ene (mw 152.24, d 1.0, 1.0 mL, 6.8 mmol, 4 eq), and $CuBr_2$ (mw 223.36, 1.52 g, 6.8 mmol, 4 eq) in ethyl acetate (~10 mL) at room temperature was stirred under argon for 20 minutes. A solution of impure title B compound (1.7 g, 30% pure, 510 mg net weight, 1.8 mmol) in chloroform (~10 mL) was added. The mixture was stirred for 18 hours, and then a mixture of concentrated aq. ammonium hydroxide/saturated aq. ammonium chloride (1:1, 200 mL) was added. This was extracted with ethyl acetate (100 mL) three times. The organic layers were combined, dried over sodium sulfate, and concentrated to yield a yellow oil (1.4 g) which was shown by NMR to be ~15% pure desired product.

$^{13}$C NMR (67.8 MHz in CDCl$_3$): δ162.4, 160.7, 154.4, 143.4, 132.5, 77.8, 51.0, 44.2, 34.5, 27.5, 19.6.

D. (R)-2-(2-Aminopropyl)-4-oxazolecarboxylic acid, methyl ester

To a solution of the title C compound (12.2 g, ~16% pure, ~2.0 g net weight, ~6.4 mmol) in methylene chloride (~15 mL) under argon was added trifluoroacetic acid (~15 mL). The resulting solution was stirred at room temperature overnight. After concentration, the residual oil was dissolved in methylene chloride (~50 mL) and washed with ~1M sodium bicarbonate. The pH of the aqueous layer was then raised to 11–12 by addition of ~1M sodium hydroxide. To the aqueous layer was added brine (~50 mL) which had been basified to pH 12 by addition of concentrated aq. sodium hydroxide. The aqueous layer was then extracted eight times with methylene chloride (~50 mL). The combined organic layers were dried over sodium sulfate and chromatographed three times on silica gel in 5% to 10% (10% concentrated aq. ammonium hydroxide/methanol)/methylene chloride to isolate pure title compound as a crystallizing brown oil (450 mg).

TLC (10% (10% concentrated aq. ammonium hydroxide/methanol)/methylene chloride): R$_f$=0.4, p-anisaldehyde, UV.

$^{13}$C NMR (67.8 MHz in CDCl$_3$): δ162.9, 161.5, 143.6, 132.8, 51.4, 44.9, 34.5, 19.6.

E. 2-[(R)-2-[[2-(3-chlorophenyl)-2-[[(1,1 dimethylethoxy)-dimethylsilyl]oxy]ethyl]amino]propyl]-4-oxazolecarboxylic acid, methyl ester To a solution of the title D compound (45 mg, mw 184, 0.24 mmol) in CD$_3$CN (~1 mL) under argon was added diisopropylethylamine (mw 129.3, d, 0.74, 42 μL, 31 mg, 0.24 mmol, 1.0 eq), and the title M compound of Example 1 (100 mg, mw 419, 0.24 mmol, 1.0 eq). The solution was heated at 40° C. for four days. The yellow solution was concentrated and chromatographed on silica gel in 2% (10% concentrated aq. ammonium hydroxide/methanol)/methylene chloride to yield pure title compound (52 mg).

TLC (5% (10% concentrated aq. ammonium hydroxide/methanol)/methylene chloride): R$_f$=0.7, p-anisaldehyde, UV.

F. 2-[(R)-2-[[2-(3-Chlorophenyl)-2-hydroxyethyl]amino]propyl]-4-oxazolecarboxylic acid, methyl ester To a solution of the title E compound (~53 mg, mw 453, 0.12 mmol) at room temperature under argon in tetrahydrofuran (~3 mL) was added acetic acid (17M, 23 μL, 0.41 mmol, 3.4 eq) and tetrabutylammonium fluoride (1M in tetrahydrofuran, 410 μL, 0.41 mmol, 3.4 eq). The solution was stirred overnight, and was then concentrated and chromatographed on silica gel in 2% (10% concentrated aq. ammonium hydroxide/methanol)/methylene chloride to isolate pure title compound (24 mg, 60% yield).

TLC (10% (10% concentrated aq. ammonium hydroxide/methanol)/methylene chloride): R$_f$=0.6, p-anisaldehyde, UV.

G. 2-[(R)-2-[[2-(3-Chlorophenyl)-2-hydroxyethyl]amino]propyl]-4oxazolecarboxylic acid To a solution of the title F compound (24 mg, mw 339, 0.07 mmol) in methanol (~1 mL) at room temperature was added aq. sodium hydroxide (~1M, 1 mL). The resulting solution was allowed to stir for two hours before addition of acetic acid (glacial, 86 μL, 1.5 mmol, 1.5 eq with respect to sodium hydroxide) and lyophilization. Chromatography on a Sep-Pak "Classic" C$_{18}$-cartridge eluting with 10% methanol/water allowed isolation of a white lyophilate (20 mg), which contained 22% acetic acid and 78% desired product.

TLC (1% acetic acid/10% methanol/89% methylene chloride): R$_f$=0.05, p-anisaldehyde, UV.

High resolution MS: observed: 325.0952 (M+H)$^+$, calculated: 325,0955 (M+H)$^+$.

EXAMPLE 7

[S-(R*,S*)]-2-[2-[(2-Hydroxy-3-phenoxypropyl)amino]propyl]-4-oxazolecarboxylic acid A. [S-(R*,S*)]-2-[2-[(2-Hydroxy-3-phenoxypropyl)amino]propyl]-4-oxazolecarboxylic acid, methyl ester To a solution of the title D compound of Example 6 (50 mg, mw 184, 0.27 mmol) in isopropanol (0.5–1.0 mL) at 0° C. under argon was added the title A compound of Example 2 (41 mg, mw 150, 0.27 mmol). After 23 days, the yellow solution was concentrated and chromatographed on silica gel in 5% (10% concentrated aq. ammonium droxide/methanol)/methylene chloride to yield pure title compound.

TLC (5% (10% concentrated aq. ammonium hydroxide/methanol)/methylene chloride): R$_f$=0.1, p-anisaldehyde, UV.

$^{13}$C NMR (67.8 MHz in CDCl$_3$): d 21.1, 35.7, 49.3, 51.9, 52.6, 68.6, 70.6, 114.9, 121.4, 129.9, 133.6, 144.3, 159.0, 162.0, 164.3.

B. [S-(R*,S*)]-2-[2-[(2-Hydroxy-3-phenoxypropyl)amino]propyl]-4-oxazolecarboxylic acid To a solution of the title A compound (45 mg, mw 334, 0.13 mmol) in methanol (~2 mL) at room temperature was added aq. sodium hydroxide (~1M, 390 μL, 0.39 mmol, 3 eq). The resulting solution was allowed to stir for three hours before addition of acetic acid (glacial, 34 μL, 0.59 mmol, 1.5 eq with respect to sodium hydroxide) and lyophilization. Chromatography on a Sep-Pak "Classic" C$_{18}$-cartridge eluting with 40% to 60% methanol/water provided the title compound as a white lyophilate (37 mg).

TLC (10% methanol/1% acetic acid/89% methylene chloride): R$_f$=0.06, p-anisaldehyde, UV.

High resolution MS: observed: 321.1462 (M+H)$^+$, calculated: 321.1450 (M+H)$^+$.

EXAMPLE 8

[S-(R*,S*)]-2-[[2-[2-[(2-Hydroxy-3-phenoxypropyl)amino]propyl]-5-thiazolyl]methyl]-2-methyl-1,3-propanedioic acid, monohydrochloride A. 2-Methyl-2-(3-oxopropyl)-1,3-propanedioic acid, diethyl ester See Warren, D. A., and Owen, A. M., *JACS* 70, 3470 (1948) for a similar Michael addition of diethyl malonate to acrolein.

To a solution of diethyl methylmalonate (mw 174, d 1.01, 68.7 mL, 69.4 g, 399 mmol) in ethanol (200 mL) at room temperature under argon was added NaOMe (mw 54, 100 mg, 1.9 mmol, 0.005 eq). The resulting solution was chilled to 0° C. Acrolein (mw 56, d 0.8, 28.0 mL, 23.5 g, 419 mmol) was added dropwise through an addition funnel over 70 minutes, with the solution maintained from 0° C. to 5° C. during the addition. The solution was stirred at 3° C. for one hour, after which time another 8.4 mL of acrolein was added over ~20 minutes. The solution was stored at 0° C. overnight before addition of acetic acid (glacial, 17.5M, 1 mL, 17.5 mmol) and concentration to a clear oil containing bits of solid. The oil was dissolved in diethyl ether (~250 mL). This was washed twice with water (250 mL). The organic layer was dried over sodium sulfate and concentrated to a clear oil (97.9 g), which was distilled, collecting the main fraction (49.7 g) at 114° C. to 118° C. at 0.9 mm Hg.

TLC (20% (95% ethanol)/hexane): $R_f=0.14$, p-anisaldehyde, UV.

$^{13}$C NMR (67.8 MHz in CDCl$_3$): $\delta$200.5, 171.4, 61.0, 52.4, 39.0, 27.4, 19.9, 13.6.

B. 2-(2-Bromo-3-oxopropyl)-2-methyl-1,3-propanedioic acid, diethyl ester

To a solution of the title A compound (mw 230, 3.0 g, 13 mmol) in diethyl ether (18 mL) and 1,4-dioxane (170 μL) at room temperature under argon was added bromine (mw 160, 100 mg, 0.63 mmol, 0.05 eq). The solution decolorized quickly and was then cooled to 0° C. Bromine (1.98 g, 12.4 mmol, 0.95 eq) was added. Two more additions of bromine (900 mg, 5.6 mmol, 0.4 eq each) were made over the next 20 minutes. The excess bromine was quenched by addition of saturated aq. sodium bicarbonate (~40 mL). The organic layer was removed and washed twice with water (40 mL), then dried over sodium sulfate and concentrated to a clear, colorless oil (4.74 g) containing 65% title compound with 34% dibrominated analogue.

TLC (35% ethyl acetate/hexane): $R_f=0.6$, p-anisaldehyde, UV.

$^{13}$C NMR (67.8 MHz in CDCl$_3$): $\delta$190.0, 170.9, 61.9, 52.8, 49.6, 37.4, 20.7, 13.7.

C. (R)-2-[[2-(2-Aminopropyl)-5-thiazolyl]methyl]-2-methyl-1,3-propanedioic acid, diethyl ester A solution of the title B compound (mw 309, 654 mg, 65% pure, net weight 425 mg, 1.38 mmol) and the title E compound of Example 1 (mw 218, 300 mg, 1.38 mmol, 1.00 eq) in dimethylformamide (~4 mL) was heated at 50° C. overnight. The dimethylformamide was distilled off at ~1 mm Hg and ~40° C. to 50° C., and the residue was chromatographed on silica gel in 20% methanol/ethyl acetate to isolate the desired product as a brown oil. The product was desalted by dissolving in methylene chloride (25 mL) and washing with 1M aq. sodium bicarbonate (~25 mL). The aqueous layer was then extracted six times with methylene chloride. The organic layers were combined, dried over sodium sulfate, and concentrated to provide the title compound (252 mg).

TLC (40% ethyl acetate/hexane): $R_f=0.05$, p-anisaldehyde, UV.

D. [S-(R*,S*)]-2-[[2-[2-[(2-Hydroxy-3-phenoxypropyl)amino]-propyl]-5-thiazolyl]methyl]-2-methyl-1,3-propanedioic acid, diethyl ester A solution of the title C compound (mw 328, 126 mg, 0.38 mmol) and the title A compound of Example 2 ((S)-(Phenoxymethyl)-oxirane) (mw 150, 57 mg, 0.38 mmol) in dimethyl sulfoxide at 60° C. under argon was stirred for five days. The solution was diluted with ethyl acetate (~20 mL) and washed twice with water (~20 mL). The organic layer was dried over sodium sulfate and concentrated to a brown oil, which was chromatographed on silica in 2% (10% concentrated aq. ammonium hydroxide/methanol)/methylene chloride to isolate pure title compound as a yellow oil (58 mg).

TLC (10% (10% concentrated aq. ammonium hydroxide/methanol)/methylene chloride): $R_f=0.5$, p-anisaldehyde, UV.

$^{13}$C NMR (67.8 MHz in CDCl$_3$): $\delta$171.7, 168.8, 159.1, 142.6, 132.2, 129.9, 121.3, 114.9, 70.6, 68.5, 60.8, 54.8, 53.8, 53.1, 49.3, 40.4, 33.3, 20.1, 14.4.

E. [S-(R*,S*)]-2-[[2-[2-[(2-Hydroxy-3-phenoxypropyl)amino]-propyl]-5-thiazolyl]methyl]-2-methyl-1,3-propanedioic acid, monohydrochloride To a solution of the title D compound (58 mg, mw 482, 0.12 mmol) in methanol (~4 mL) at room temperature was added aq. sodium hydroxide (~1M, 1200 μL, 0.12 mmol, 10 eq). The resulting solution was stirred for 60 hours before lyophilization, acidification to pH 1 with 1M aqueous hydrochloric acid, and relyophilization. Chromatography on a Sep-Pak C$_{18}$ (5 g) cartridge, eluting with water to remove inorganics and then with 40% methanol/water to elute desired product, provided the title compound as a white lyophilate (15 mg).

TLC (10% (10% concentrated aq. ammonium hydroxide/methanol)2% trifluoroacetic acid/88% methylene chloride): $R_f=0.10$, p-anisaldehyde, UV.

High resolution MS: observed: 423.1580 (M+H)$^+$, calculated: 423.1590 (M+H)$^+$.

EXAMPLE 9

[S-(R*,S*)]-2-[2-[(2-Hydroxy-3-phenoxypropyl)amino]-propyl]-5-thiazolebutanoic acid, 0.4 sodium salt A. 6-Oxohexanoic acid, ethyl ester See Huckstep, M. et al., *Synthesis*, 881 (1982) for synthesis of a similar aldehyde using this chemistry. See Ghana, M. et al., *JCS Perkin Trans.* 1, 2963 (1988) for information regarding the support of pyridinium chlorochromate on Florisil.

To a solution of caprolactone monomer (mw 114, 11.4 g, 0.100 mol) in ethanol (200 proof, 200 mL) was added sulfuric acid (concentrated, 10 drops). The mixture was allowed to reflux for four hours, and was then stored at room temperature under argon overnight. The solution was neutralized by addition of sodium bicarbonate (1 g). The mixture was stirred for about 10 minutes, then filtered. The filtrate was concentrated to a clear oil.

To a solution of pyridinium chlorochromate (mw 215, 41.0 g, 190.7 mmol, 1.9 eq) in methylene chloride (400 mL) at room temperature under argon was added Florisil (~50 g). The resulting mixture was allowed to stir for 15 to 20 minutes until the pyridinium chlorochromate seemed to be evenly distributed on the Florisil, as judged by the uniform rusty brown color of the mixture. The oil made above was added as a solution in methylene chloride (~200 mL). Some warming of the reaction mixture was noted. The mixture was allowed to stir for one hour, followed by dilution with ether (~200 mL). The mixture was filtered through a 6"×4" Florisil pad (ether rinse). The filtrate was partially concentrated and then filtered through another Florisil pad of the same size (ether rinse) to remove the final traces of oxidant. This filtrate was concentrated into a green oil and then passed through a 3"×2" pad of silica gel, eluting with 50% ethyl acetate/hexane. The eluant was concentrated to a green oil (13.6 g). TLC (50% ethyl acetate/hexane): $R_f=0.7$, p-anisaldehyde.

$^{13}$C NMR (67.8 MHz in CDCl$_3$) $\delta$201.7, 172.8, 59.7, 42.3, 33.6, 23.8, 21.0, 13.7.

B. 5-Bromo-6-oxohexanoic acid, ethyl ester

See U.S. Pat. No. 4,053,618 for similar chemistry.

To a solution of the title A compound (mw 158, 2.9 g, ~95% pure, 2.8 g net, 17.5 mmol) in ether (24 mL) and 1,4-dioxane (2.4 mL) at room temperature was added bromine (mw 160, 140 mg, 0.88 mmol, 0.05 eq). The solution was cooled to 0° C. and then more bromine (1.26 g, 7.88 mmol, 0.5 eq) was added. The solution decolorized over ~20 minutes. The reaction solution was washed three times with ~50 mL of ~1.5M aq. sodium bicarbonate. The organic layer was dried over sodium sulfate, and then concentrated to a colorless oil (3.04 g) which was shown to be impure desired product.

TLC (50% ethyl acetate/hexane): $R_f$=0.8, PMA.

C. (R)-2-(2-Aminopropyl)-5-thiazolebutanoic acid, ethyl ester

To a solution of the title E compound of Example 1 ((R)-3-[[(1,1-dimethylethoxy)carbonyl]amino]butanethioamide (mw 218, 0.50 g, 2.29 mmol) in dimethylformamide (2 mL) was added the title B compound (impure, ~1 g). The solution was heated at 60° C. under argon for two days, at which point another aliquot of impure title B compound (~1 g) was added. The solution was heated for another three days at 60° C., and then at 80° C. for two days. The solution was then cooled and chromatographed in 2 to 10% (10% concentrated aq. ammonium hydroxide/methanol)/methylene chloride to isolate a brown oil (133 mg), which was pure desired product.

TLC (10% (10% concentrated aq. ammonium hydroxide/methanol)/methylene chloride): $R_f$=0.5, p-anisaldehyde, UV.

$^{13}$C NMR (67.8 MHz in CDCl$_3$) δ172.8, 166.3, 139.3, 137.9, 60.3, 47.5, 41.7, 33.1, 26.4, 26.0, 22.3, 14.1.

D. [S-(R*,S*)]-2-[2-[[2-Hydroxy-3-phenoxypropyl)amino]-propyl]-5-thiazolebutanoic acid, ethyl ester A solution of the title A compound of Example 2 ((S)-(phenoxymethyl)oxirane) (mw 150, 78 mg, 0.52 mmol) and the title C compound (mw 256, 133 mg, 0.52 mmol) was prepared neat and heated at 60° C. for two days. The solution was then chromatographed in 5 to 20% (10% concentrated aq. ammonium hydroxide/methanol)/methylene chloride to isolate a brown oil (100 mg), pure title compound.

TLC (10% (10% concentrated aq. ammonium hydroxide/methanol)/methylene chloride): $R_f$=0.6, p-anisaldehyde, UV.

$^{13}$C NMR (67.8 MHz in CDCl$_3$) δ173.0, 166.7, 158.5, 138.9, 137.9, 129.3, 120.8, 114.4, 70.1, 68.0, 60.4, 52.6, 50.2, 48.8, 39.8, 33.1, 26.0, 20.0, 14.1.

E. [S-(R*,S*)]-2-[2-[(2-Hydroxy-3-phenoxypropyl)amino]propyl]-5-thiazolebutanoic acid, 0.4 sodium salt To a solution of the title D compound (100 mg, mw 406, 0.25 mmol) in 95% ethanol (~10 mL) at room temperature was added aq. sodium hydroxide (~1M, 0.5 mL, 0.5 mmol, 2 eq). The resulting solution was allowed to stir overnight. The reaction solution was lyophilized and then purified on a Sep-Pak C$_{18}$ cartridge (1 g), eluting with 50% methanol/water to isolate pure title compound as a white lyophilate (90 mg).

TLC (1% acetic acid/99% [10% (10% concentrated aq. ammonium hydroxide/methanol)/methylene chloride]): $R_f$=0.3, p-anisaldehyde, UV.

High resolution MS: observed: 379.1688 (M+H)$^+$, calculated: 379.1691 (M+H)$^+$.

EXAMPLE 10

2-[(R)-2-[[2-(3-Chlorophenyl)-2-hydroxyethyl]amino]propyl]-5-thiazolebutanoic acid, 0.6 sodium salt

A. (R)-2-[2-[[2-(3-Chlorophenyl)-2-[[(1,1-dimethylethyl)-dimethylsilyl]oxy]ethyl]amino]propyl]-5-thiazolebutanoic acid, ethyl ester To a solution of the title M compound of Example 1 (3-chloro-β-[[(1,1-dimethylethyl)dimethylsilyl]oxy]-benzeneethanol, (trifluoromethyl)sulfonate) (mw 419, 261 mg, 0.63 mmol) and the title C compound of Example 9 ((R)-2-(2-Aminopropyl)-5-thiazolebutanoic acid, ethyl ester) (mw 256, 160 mg, 0.63 mmol) in MeCN (~4 mL) under argon at room temperature was added diisopropylethylamine (mw 129, d 0.74, 0.63 mmol, 110 μL, 1 eq). The solution was allowed to stir for two days, at which point it was chromatographed in 3% (10% concentrated aq. ammonium hydroxide/methanol)/methylene chloride to isolate pure title compound as a brown oil (200 mg).

TLC (10% (10% concentrated aq. ammonium hydroxide/methanol)/methylene chloride): $R_f$=0.8, p-anisaldehyde, UV.

B. (R)-2-[2-[[2-(3-Chlorophenyl)-2-hydroxyethyl]amino]-propyl]-5-thiazolebutanoic acid, ethyl ester To a solution of the title A compound (mw 525, 200 mg, 0.38 mmol) in tetrahydrofuran (~3 mL) under argon at room temperature was added tetrabutylammonium fluoride (Aldrich, 1.0M in tetrahydrofuran, 1.0 mL, 1.0 mmol, 2.6 eq). The resulting solution was allowed to stir for 60 hours, after which time it was chromatographed in 5% (10% concentrated aq. ammonium hydroxide/methanol)/methylene chloride to isolate a brown oil (125 mg) which was shown to be pure title compound by NMR.

TLC (5% (10% concentrated aq. ammonium hydroxide/methanol)/methylene chloride): $R_f$=0.25, p-anisaldehyde, UV.

C. 2-[(R)-2-[[2-(3-Chlorophenyl)-2-hydroxyethyl]amino]propyl]-5-thiazolebutanoic acid, 0.6 sodium salt To a solution of the title B compound (125 mg, mw 411, 0.30 mmol) in 95% ethanol (~2 mL) at room temperature was added aq. sodium hydroxide (~1M, 0.6 mL, 0.6 mmol, 2 eq). The resulting solution was allowed to stir for three hours. The reaction solution was lyophilized and then purified on a Sep-Pak C$_{18}$ cartridge (1 g), eluting with 50% methanol/water to isolate pure title compound as a white lyophilate (97 mg).

TLC (1% acetic acid/99% [10% (10% concentrated aq. ammonium hydroxide/methanol)/methylene chloride]): $R_f$=0.05, p-anisaldehyde, UV.

High resolution MS: observed: 405.1023 (M+H)$^+$, calculated: 405.1016 (M+H)$^+$.

What is claimed is:

1. A compound of the formula

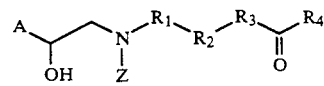

I or a pharmaceutically acceptable salt thereof where

A is 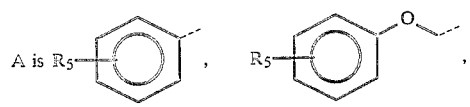, 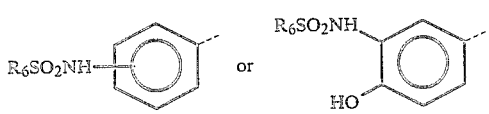,

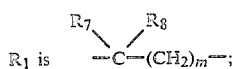 or 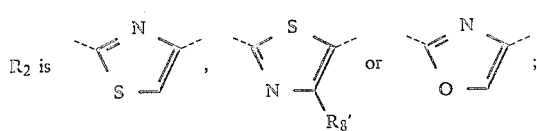;

$R_1$ is 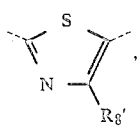;

$R_2$ is 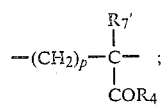;

$R_3$ is $-(CH_2)_n-$; or in the case where $R_2$ is

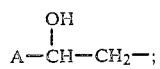, $R_3$ is $-(CH_2)_n-$ or

;

$R_4$ is hydroxy, alkoxy, amino, alkylamino or dialkylamino;

$R_5$ is hydrogen, fluorine, chlorine, bromine, iodine, $-CN$, $-CF_3$, lower alkyl, lower alkoxy, cycloalkyl or aryl;

$R_6$ is lower alkyl, cycloalkyl or aryl;

$R_7$, $R_7'$, $R_8$ and $R_8'$, are independently hydrogen or lower alkyl or $R_7$ and $R_8$ may together be $CH_2CH_2$;

Z is hydrogen or

;

m is an integer of 1 or 2;
n is zero or an integer of 1 to 6; and
p is an integer of 1 to 5.

2. The compound as recited in claim 1 wherein A is

, $R_2$ is

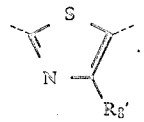, and $R_3$ is $-(CH_2)_n-$.

3. The compound as recited in claim 1 wherein A is

, and $R_2$ is

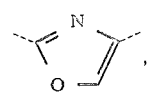.

4. The compound as recited in claim 1 wherein A is

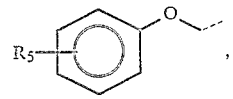, $R_2$ is

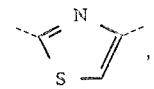, and $R_3$ is $-(CH_2)_n-$.

5. The compound as recited in claim 1 wherein A is

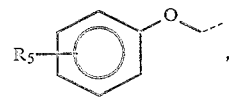, $R_2$ is

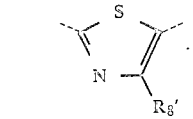, and $R_3$ is $-(CH_2)_n-$.

6. The compound as recited in claim 1 wherein A is

7. The compound as recited in claim 1 wherein A is

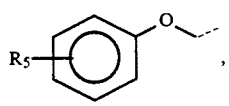

$R_2$ is

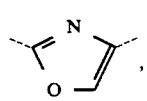

and $R_3$ is —$(CH_2)_n$—.

8. The compound as recited in claim 1 wherein A is

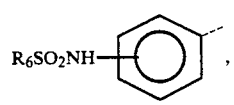

$R_2$ is

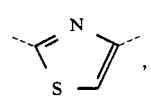

and $R_3$ is —$(CH_2)_n$—.

9. The compound as recited in claim 1 wherein A is

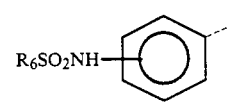

and $R_2$ is

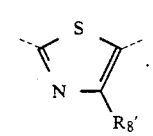

10. The compound as recited in claim 1 wherein A is

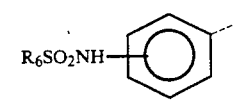

$R_2$ is

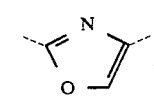

and $R_3$ is —$(CH_2)_n$—.

11. The compound as recited in claim 1 wherein A is

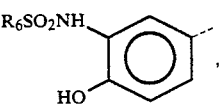

$R_2$ is

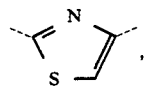

and $R_3$ is —$(CH_2)_n$—.

12. The compound as recited in claim 1 wherein A is

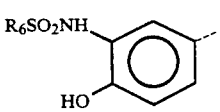

and $R_2$ is

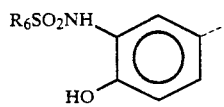

13. The compound as recited in claim 1 wherein A is

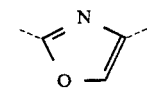

$R_2$ is and $R_3$ is —$(CH_2)_n$—.

14. The compound as recited in claim 1, 2-[(R)-2-[[2-(3-Chlorophenyl)-2-hydroxyethyl]amino]propyl]-4-thiazolecarboxylic acid, or a pharmaceutically acceptable salt thereof.

15. The compound as recited in claim 1, [S-(R*,S*)]-2-[2-[(2-Hydroxy-3-phenoxypropyl)amino]propyl]-4-thiazolecarboxylic acid, or a pharmaceutically acceptable salt thereof.

16. The compound as recited in claim 1, [S-(R*,S*)]-2-[2-[(2-Hydroxy-3-phenoxypropyl)amino]propyl]-5-thiazolepropanoic acid, or a pharmaceutically acceptable salt thereof.

17. The compound as recited in claim 1, [2R-[2R*(S*,S*)]]-2-[2-[Bis-(2-hydroxy-3-phenoxy-propyl)amino]propyl]-5-thiazolepropanoic acid, or a pharmaceutically acceptable salt thereof.

18. The compound as recited in claim 1, 2-[(R)-2-[[2-(3-Chlorophenyl)-2-hydroxyethyl]amino]propyl]-5-thiazolepropanoic acid, or a pharmaceutically acceptable salt thereof.

19. The compound as recited in claim 1, 2-[(R)-2-[[2-(3-Chlorophenyl)-2-hydroxyethyl]amino]propyl]-4-oxazolecarboxylic acid, or a pharmaceutically acceptable salt thereof.

20. The compound as recited in claim 1, [S-(R*,S*)]-2-[2-[(2-Hydroxy-3-pheoxypropyl)amino]propyl]-4-oxazolecarboxylic acid, or a pharmaceutically acceptable salt thereof.

21. The compound as recited in claim 1, [S-(R*,S*)]-2-[[2-[2-[2-Hydroxy-3-phenoxypropyl)amino]propyl]-5-thiazolyl]methyl]-2-methyl-1,3-propanedioic acid, monohydrochloride, or a pharmaceutically acceptable salt thereof.

22. The compound as recited in claim 1, [S-(R*,S*)]-2-[2-[(2-Hydroxy-3-phenoxypropyl)amino]propyl]-5-thiazolebutanoic acid or a pharmaceutically acceptable salt thereof.

23. The compound as recited in claim 1, 2-[(R)-2-[[2-(3-Chlorophenyl)-2-hydroxyethyl]amino]propyl]-5-thiazolebutanoic acid, or a pharmaceutically acceptable salt thereof.

24. A pharmaceutical composition comprising a compound of claim 1 and a pharmaceutically acceptable carrier.

25. A method for treating diabetes comprising administering to a mammalian specie in need thereof a therapeutically effective amount of a composition of claim 24.

26. A method for treating obesity comprising administering to a mammalian specie in need thereof a therapeutically effective amount of a composition of claim 24.

27. A method for treating intestinal hypermotility comprising administering to a mammalian specie in need thereof a therapeutically effective amount of a composition of claim 24.

28. A pharmaceutical composition comprising a compound of claim 1 in combination with a beta$_1$ or beta$_2$ adrenergic blocker or stimulant and a pharmaceutically acceptable carrier.

29. A method for treating diabetes comprising administering to a mammalian specie in need thereof a therapeutically effective amount of a composition of claim 28.

30. A method for treating obesity comprising administering to a mammalian specie in need thereof a therapeutically effective amount of a composition of claim 28.

31. A method for treating gastrointestinal diseases comprising administering to a mammalian specie in need thereof a therapeutically effective amount of a composition of claim 28.

* * * * *